United States Patent
Toyoda et al.

(10) Patent No.: US 10,445,875 B2
(45) Date of Patent: Oct. 15, 2019

(54) PATTERN-MEASURING APPARATUS AND SEMICONDUCTOR-MEASURING SYSTEM

(71) Applicant: Hitachi High-Technologies Corporation, Minato-ku, Tokyo (JP)

(72) Inventors: Yasutaka Toyoda, Tokyo (JP); Norio Hasegawa, Tokyo (JP); Takeshi Kato, Tokyo (JP); Hitoshi Sugahara, Tokyo (JP); Yutaka Hojo, Tokyo (JP); Daisuke Hibino, Tokyo (JP); Hiroyuki Shindo, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 2 days.

(21) Appl. No.: 15/964,559

(22) Filed: Apr. 27, 2018

(65) Prior Publication Data

US 2018/0247400 A1    Aug. 30, 2018

Related U.S. Application Data

(63) Continuation of application No. 14/768,600, filed as application No. PCT/JP2014/052611 on Feb. 5, 2014, now Pat. No. 9,990,708.

(30) Foreign Application Priority Data

Feb. 20, 2013  (JP) .................. 2013-030547

(51) Int. Cl.
*G06T 7/00* (2017.01)
*H01J 37/22* (2006.01)
(Continued)

(52) U.S. Cl.
CPC .......... *G06T 7/001* (2013.01); *G01N 23/225* (2013.01); *G01N 23/2251* (2013.01);
(Continued)

(58) Field of Classification Search
CPC ......... G01N 2223/6113; G01N 23/225; G01N 23/2251; G06T 2207/10061;
(Continued)

(56) References Cited

U.S. PATENT DOCUMENTS 5,995,219 A   11/1999  Tabata
7,071,468 B2   7/2006  Miyai et al.
(Continued)

FOREIGN PATENT DOCUMENTS

JP    5-60533 A    3/1993
JP    10-247245 A  9/1998
(Continued)

OTHER PUBLICATIONS

International Search Report (PCT/ISA/210) dated May 13, 2014 with English translation (nine pages).

*Primary Examiner* — Kim Y Vu
*Assistant Examiner* — Michael J Vanchy, Jr.
(74) *Attorney, Agent, or Firm* — Crowell & Moring LLP

(57) ABSTRACT

A pattern-measuring apparatus and a semiconductor-measuring system are provided which are able to obtain an evaluation result for suitably selecting processing with respect to a semiconductor device. In particular, there is proposed a pattern-measuring apparatus including an arithmetic device which compares a circuit pattern of an electronic device with a reference pattern, in which the arithmetic device classifies the circuit pattern in processing unit of the circuit pattern on the basis of a comparison of a measurement result between the circuit pattern and the reference pattern with at least two threshold values.

7 Claims, 15 Drawing Sheets

(51) Int. Cl.
  *G01N 23/2251* (2018.01)
  *H01J 37/28* (2006.01)
  *H01L 21/66* (2006.01)
  *G01N 23/225* (2018.01)

(52) U.S. Cl.
  CPC ............ *H01J 37/222* (2013.01); *H01J 37/28* (2013.01); *H01L 22/12* (2013.01); *G01N 2223/6113* (2013.01); *G06T 2207/10061* (2013.01); *G06T 2207/30148* (2013.01); *H01J 2237/221* (2013.01); *H01J 2237/2817* (2013.01)

(58) Field of Classification Search
  CPC .......... G06T 2207/30148; G06T 7/001; G06T 7/0006; H01J 2237/221; H01J 2237/2817; H01J 37/222; H01J 37/28; H01L 22/12; H01L 22/20; G03F 1/84; G03F 7/706; G06F 17/5068
  See application file for complete search history.

(56) References Cited

U.S. PATENT DOCUMENTS

| | | |
|---|---|---|
| 7,796,801 B2 | 9/2010 | Kitamura et al. |
| 8,019,161 B2 | 9/2011 | Morokuma et al. |
| 2002/0164065 A1* | 11/2002 | Cai .................. G01N 21/95607 382/149 |
| 2003/0018406 A1* | 1/2003 | Yoshitake ............ G03F 7/70125 700/121 |
| 2004/0015808 A1* | 1/2004 | Pang ........................ G03F 1/84 716/52 |
| 2006/0271907 A1* | 11/2006 | Izuha .................. G06F 17/5031 716/52 |
| 2008/0286667 A1 | 11/2008 | Okita |
| 2009/0144691 A1* | 6/2009 | Rathsack ................ H01L 22/20 716/56 |
| 2009/0180680 A1 | 7/2009 | Satou et al. |
| 2009/0208090 A1* | 8/2009 | Nishiura .............. G06K 9/6255 382/149 |
| 2009/0214103 A1* | 8/2009 | Tanaka .................... G06T 7/001 382/145 |
| 2009/0231424 A1* | 9/2009 | Honda .................. G06T 7/0006 348/87 |

FOREIGN PATENT DOCUMENTS

| | | |
|---|---|---|
| JP | 2004-163420 A | 6/2004 |
| JP | 2007-248087 A | 9/2007 |
| JP | 2009-170606 A | 7/2009 |
| WO | WO 2007/086316 A1 | 8/2007 |

* cited by examiner

[Fig. 1]
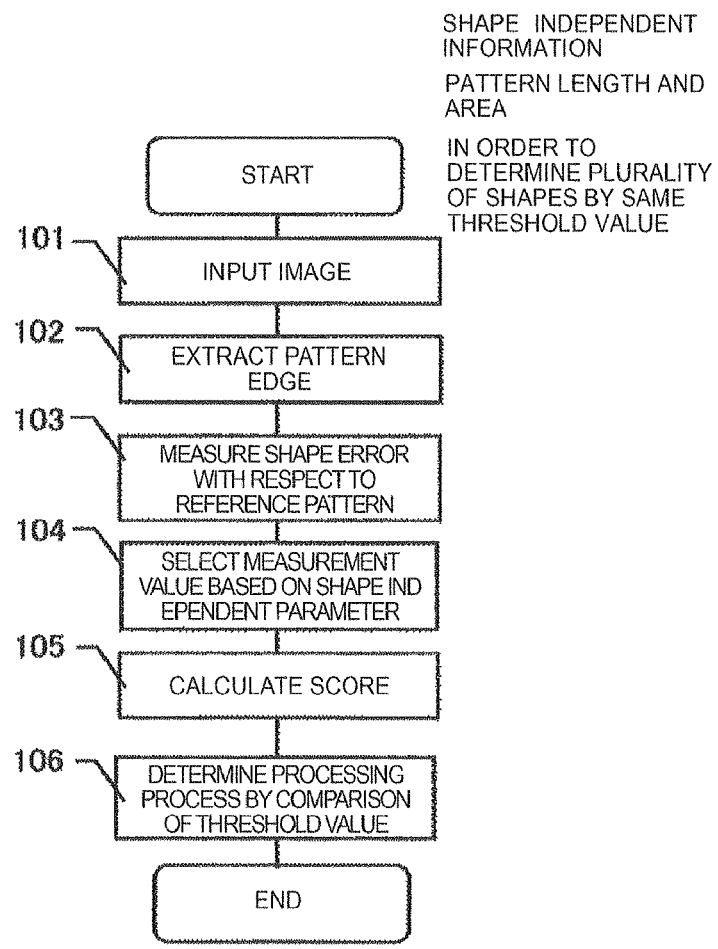

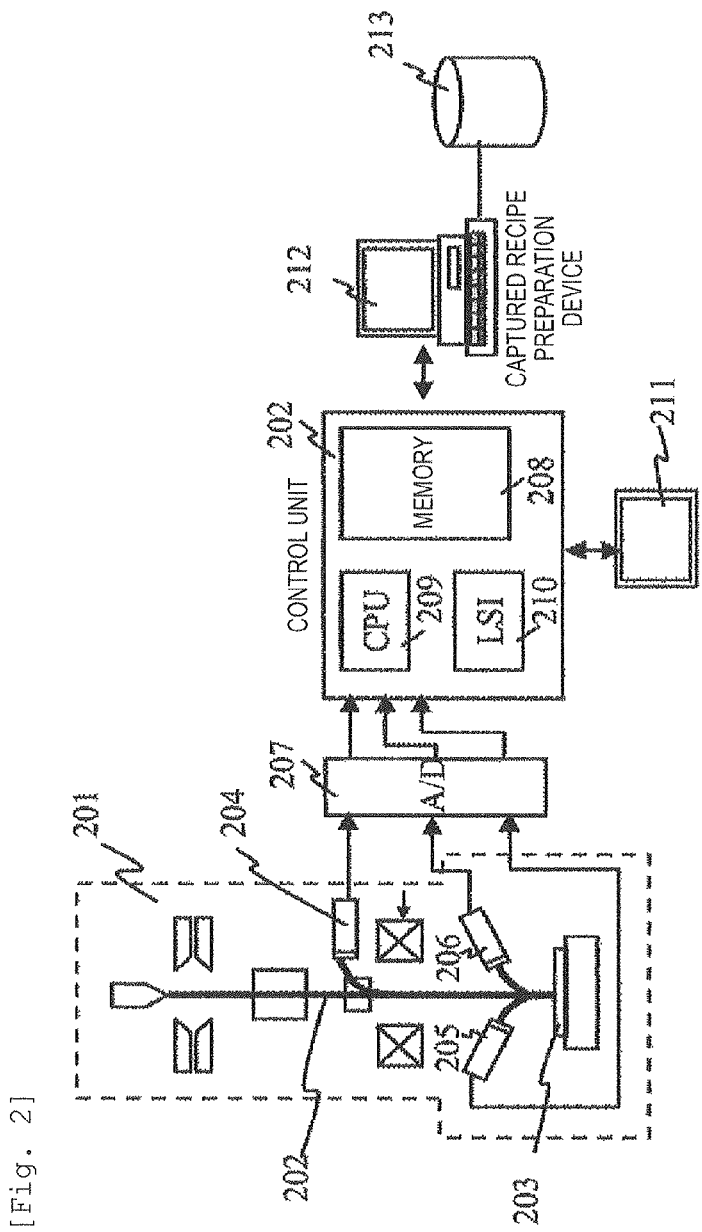
[Fig. 2]

[Fig. 3]
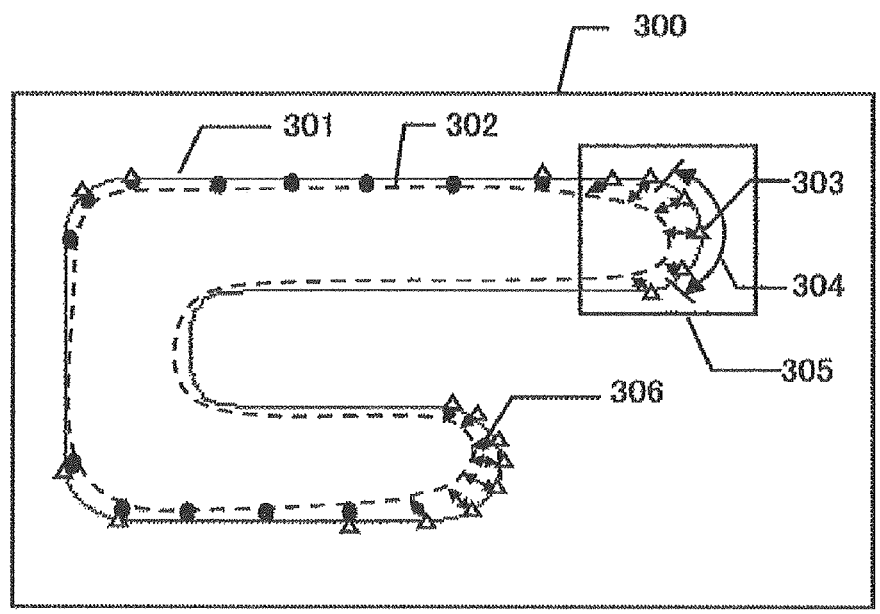
EPE IN RANGE OF L nm BASED ON MAXIMUM POINT
EPE IN M*N AREA RANGE BASED ON MAXIMUM POINT
EPE IN WHICH OUTLINE LENGTH FROM MAXIMUM POINT REACHES L nm

[Fig. 4]
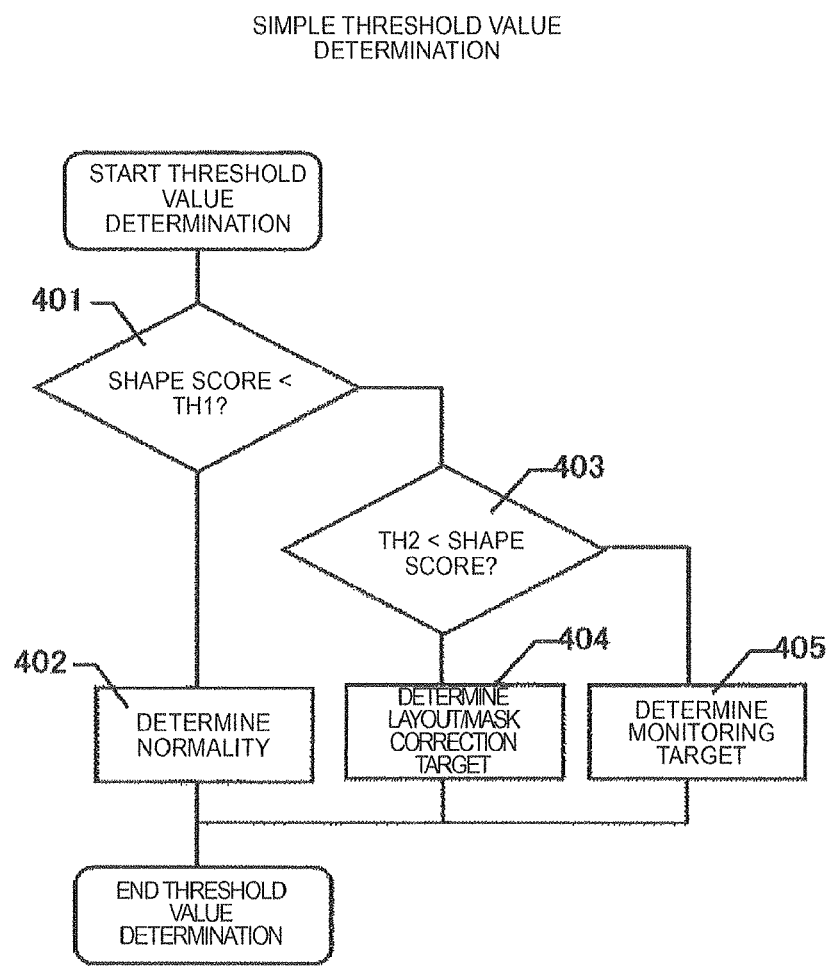

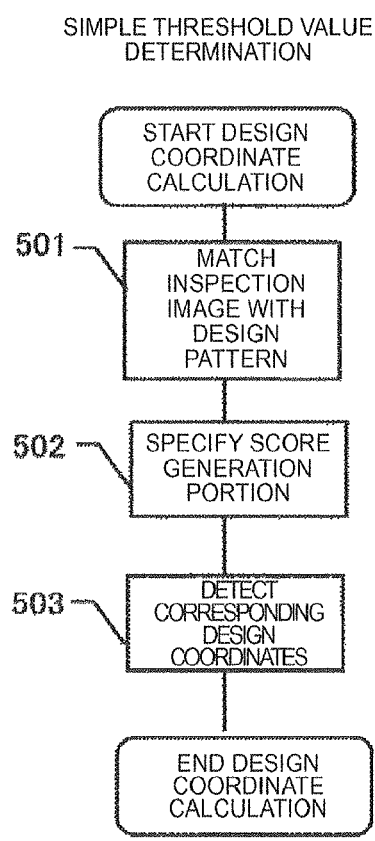
[Fig. 5]

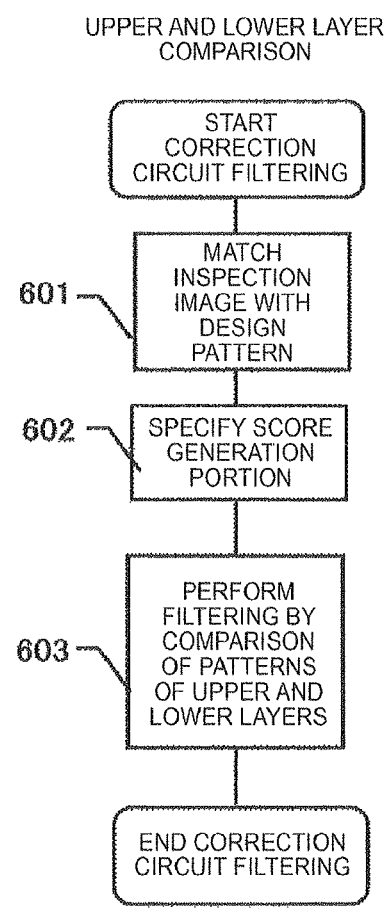
[Fig. 6]

[Fig. 7]
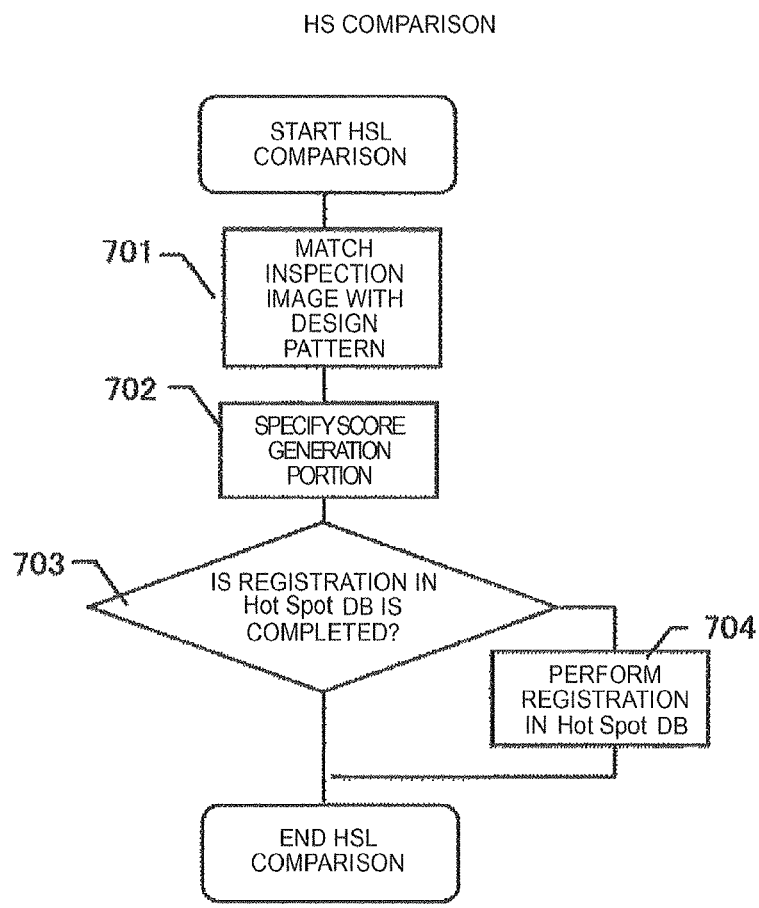

[Fig. 8A] [Fig. 8B]
UPPER AND LOWER
LAYER COMPARISON
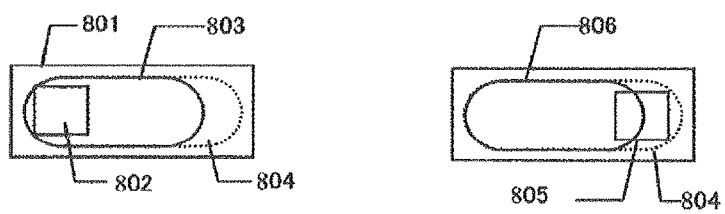
COMPARISON WITH HSL
[Fig. 9A] [Fig. 9B]
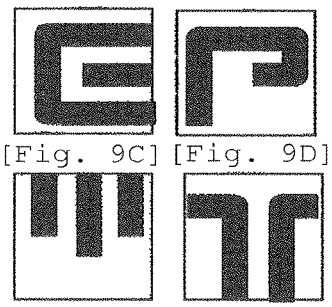
[Fig. 9C] [Fig. 9D]
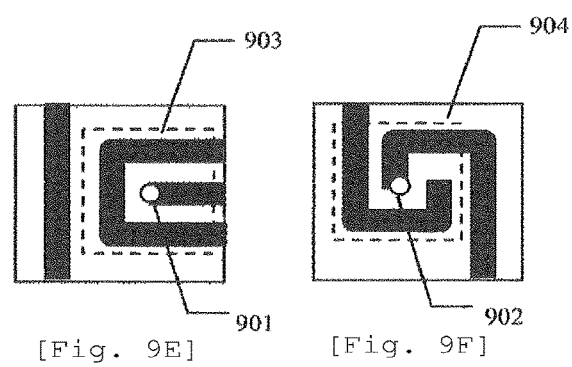
[Fig. 9E] [Fig. 9F]

[Fig. 10]
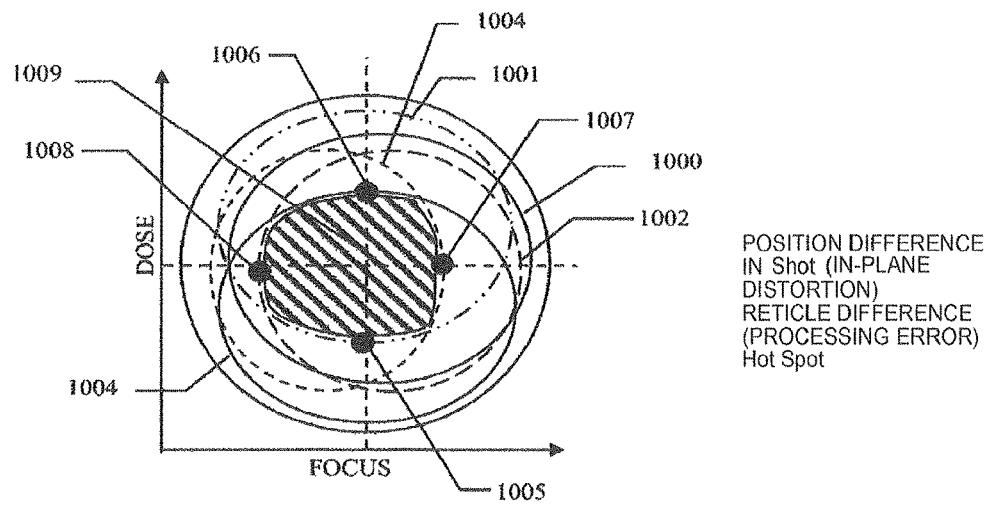
POSITION DIFFERENCE
IN Shot (IN-PLANE
DISTORTION)
RETICLE DIFFERENCE
(PROCESSING ERROR)
Hot Spot
[Fig. 11]
PWA EVALUATION
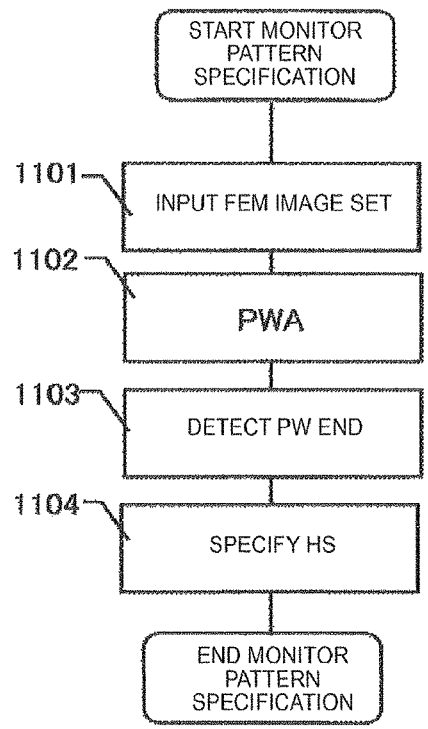

[Fig. 12]
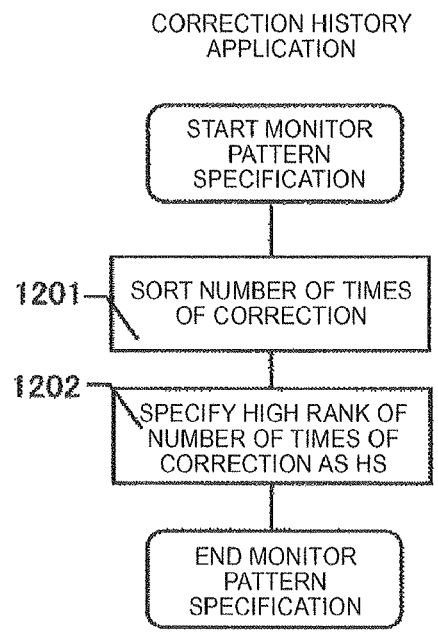
[Fig. 13]
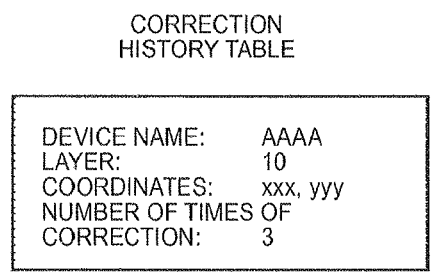

[Fig. 14]
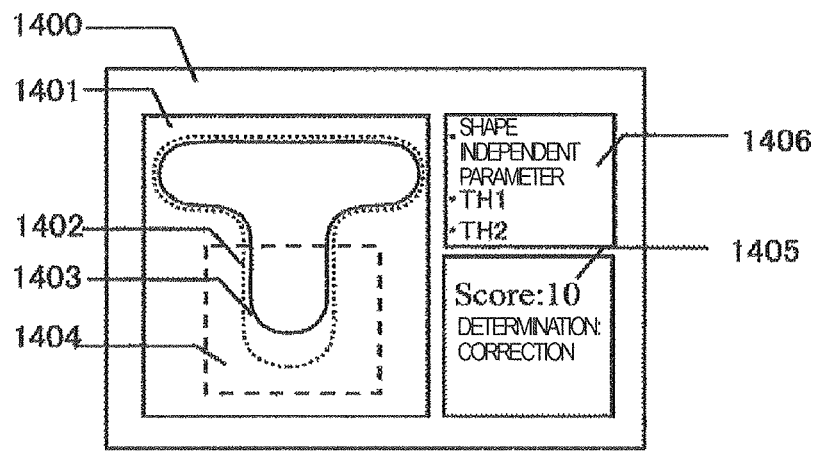
[Fig. 15]
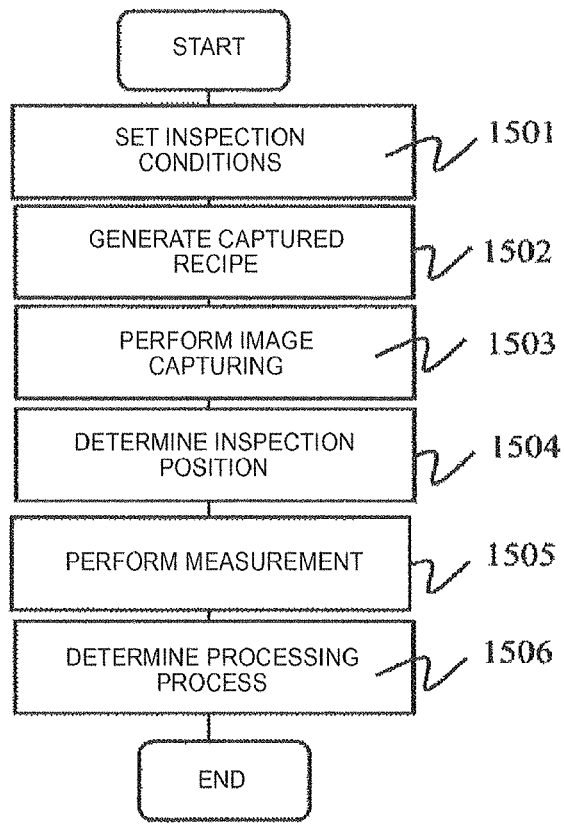

[Fig. 16]
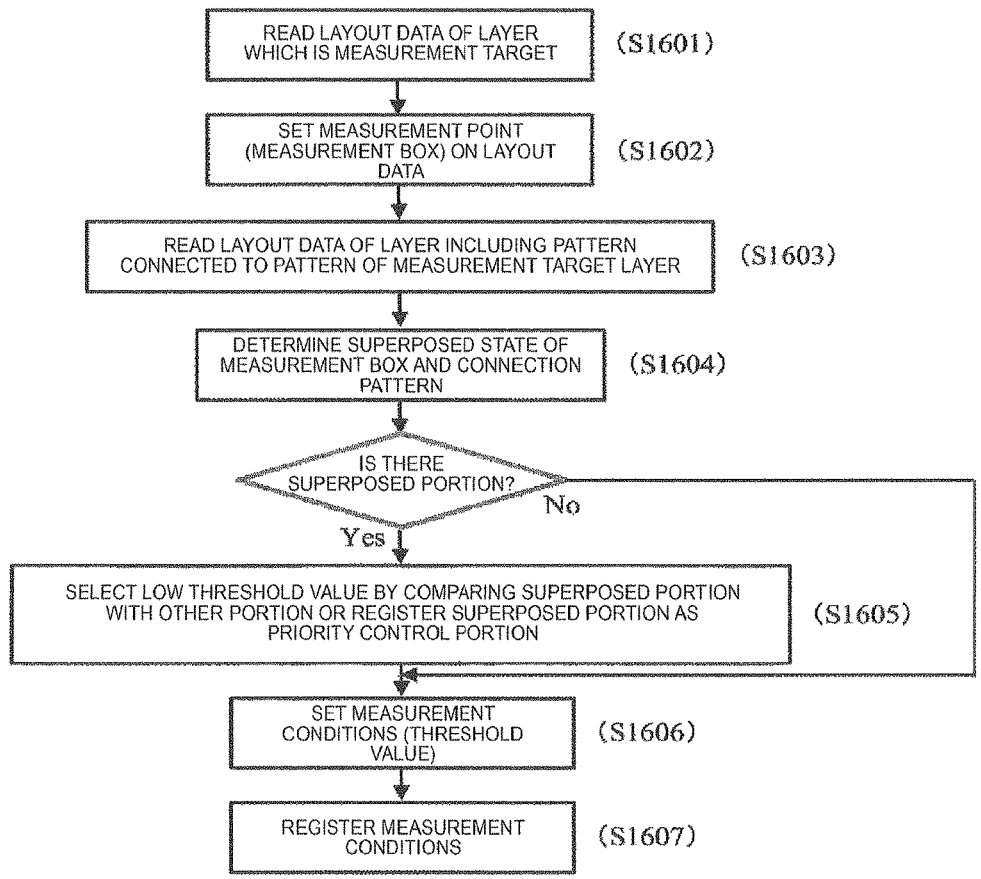

[Fig. 17A]
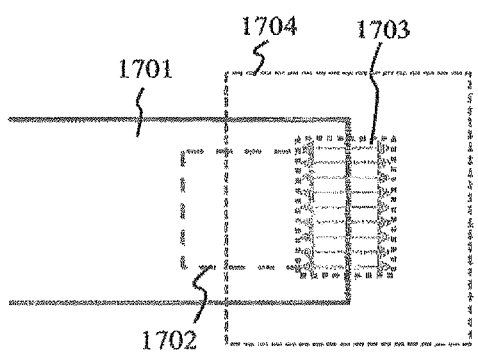
[Fig. 17B]
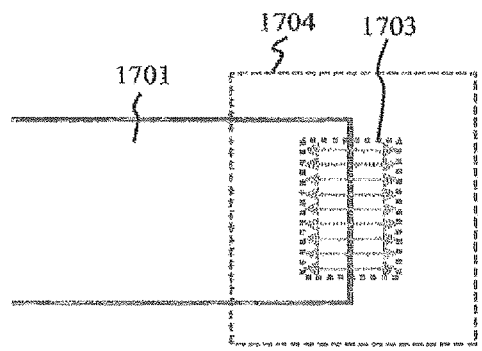

[Fig. 18]
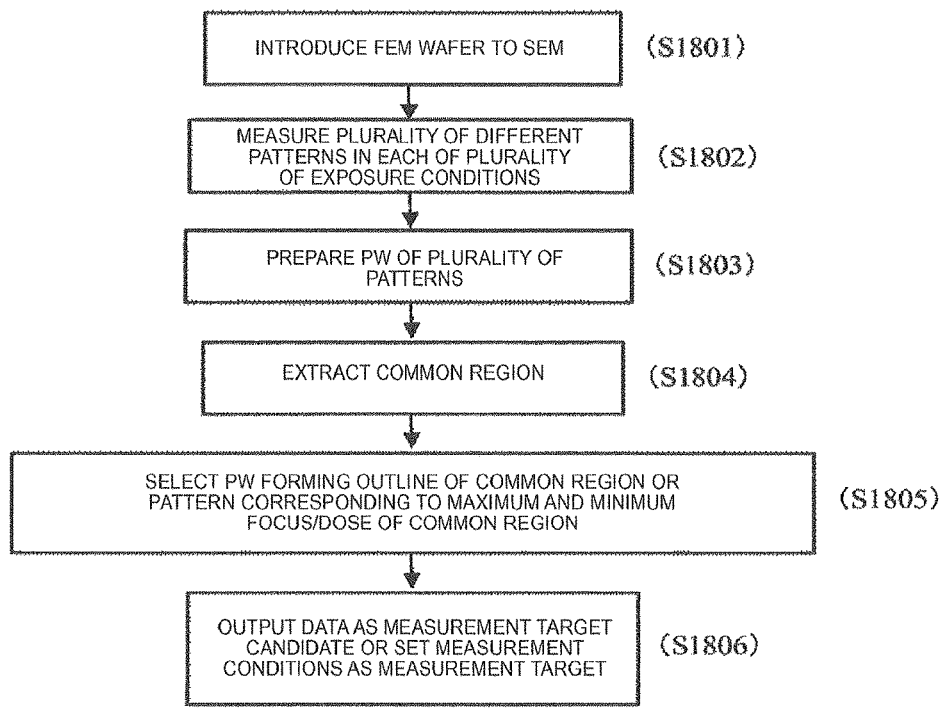

[Fig. 19]
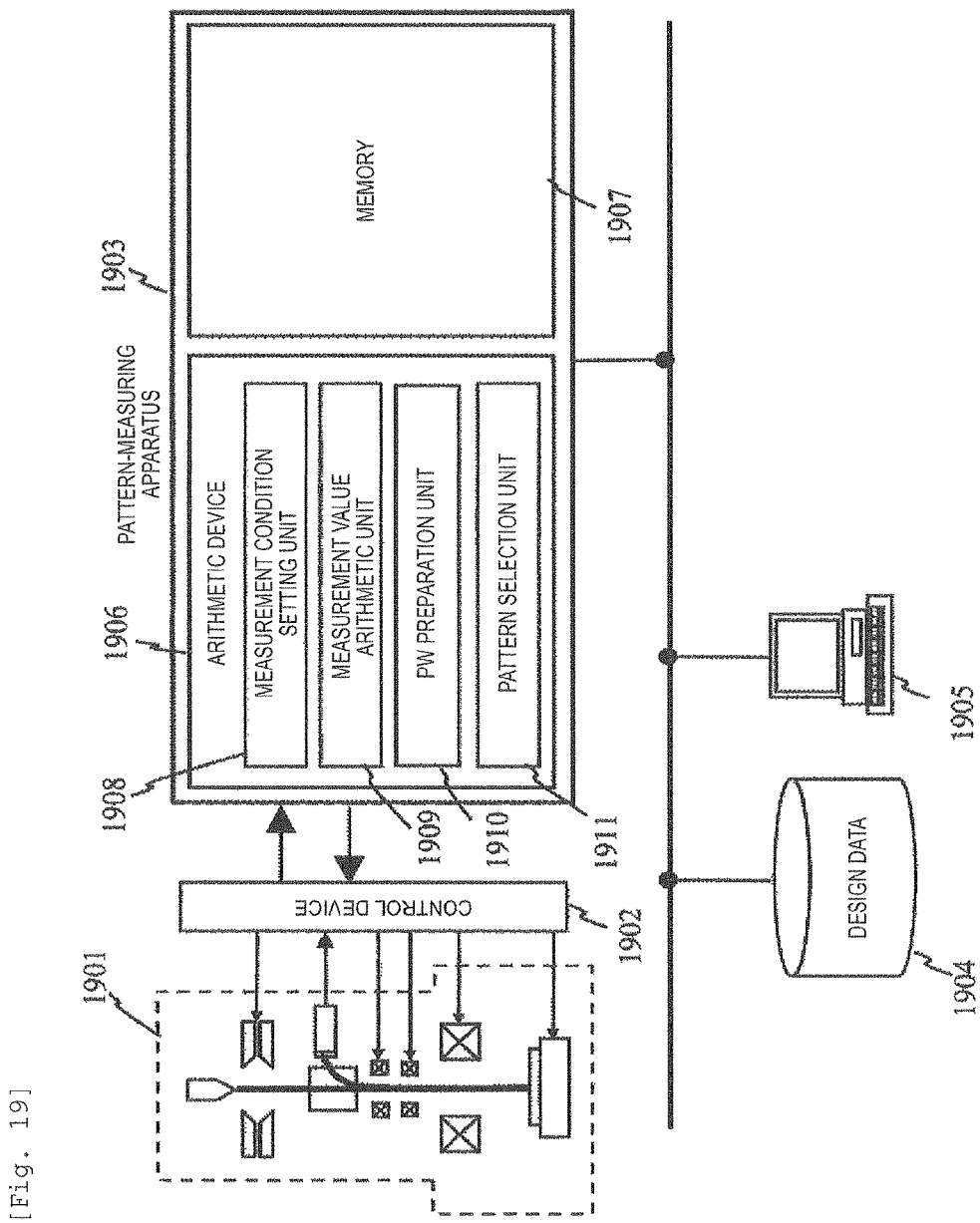

PATTERN-MEASURING APPARATUS AND SEMICONDUCTOR-MEASURING SYSTEM

CROSS REFERENCE TO RELATED APPLICATIONS

This application is a continuation of U.S. application Ser. No. 14/768,600, filed Aug. 18, 2015, which is a National Stage of PCT International Application No. PCT/JP2014/052611, filed Feb. 5, 2014, which claims priority under 35 U.S.C. § 119 from Japanese Patent Application No. 2013-030547, filed Feb. 20, 2013, the entire disclosures of which are herein expressly incorporated by reference.

TECHNICAL FIELD

The present invention relates to a pattern-measuring apparatus measuring an electronic device, and in particular, relates to a pattern-measuring apparatus and a semiconductor-measuring system, which compare a circuit pattern of an electronic device with a reference pattern, and determine a processing process of the circuit pattern.

BACKGROUND ART

Recently, a semiconductor has been miniaturized and multi-layered, and the logic has been also complicated, and thus it is extremely difficult to manufacture the semiconductor. As a result thereof, a defect due to a manufacturing process tends to be increased, and thus it is important to accurately inspect such a defect. A review SEM and a CD-SEM is used for specifically inspecting and measuring such a defect. These SEMs inspect or measure target coordinates based on optical simulation, and a circuit pattern corresponding to target coordinates based on an inspection result of an optical inspection device. As an inspection or measurement method, various methods have been proposed, and in particular, in a manufacturing process of a semiconductor after 65 nm, a method of detecting the defect by comparing the shape with a reference pattern (PTL 1 and PTL 2) has been used in order to accurately grasp a state of the defect due to an optical proximity effect.

The comparison of the shape with the reference pattern is performed by the following procedure. First, an operator defines a circuit pattern having a preferred shape as a reference pattern. As the reference pattern, a golden pattern or the like which is selected by an inspection operator from a circuit pattern generated by simulating design data or a circuit pattern to be actually manufactured and a manufactured circuit pattern is used. Next, the circuit pattern is extracted from a captured image by using edge detection processing or the like. Next, the reference pattern and the circuit pattern are superposed. The superposition is manually adjusted or automatically adjusted by pattern matching. The shape of the circuit pattern is deformed into various shapes according to manufacturing conditions of the semiconductor or a circuit layout. In PTL 2, for this reason, in order to accurately grasp the degree of deformation, a measurement region is set in a two-dimensional region including inspection coordinates, and a distance between the reference pattern included in the measurement region and the edge of the circuit pattern is cyclopaedically measured at predetermined intervals. Next, a plurality of measurement values obtained from the measurement region are averaged, the result thereof is set to the measurement value of the measurement region, the normality or the defect of the circuit pattern is determined by a comparison with respect to a predetermined threshold value, and the circuit pattern including the defect is subjected to a process of circuit design and mask correction.

CITATION LIST

Patent Literature

PTL 1: JP-A-2004-163420 (corresponding U.S. Pat. No. 7,796,801)

PTL 2: JP-A-2007-248087 (corresponding U.S. Pat. No. 8,019,161)

SUMMARY OF INVENTION

Technical Problem

According to the measurement method as disclosed in PTL 1 and PTL 2, it is possible to specify a two-dimensional shape difference between the design data (layout data) and actual pattern data, but when the average value of the plurality of measurement values obtained by comparing the reference pattern existing in the predetermined measurement region with the edge of the circuit pattern is set to the measurement value, the measurement value is changed due to a ratio of a normal portion of the circuit pattern existing in the measurement region and a ratio of an abnormal portion.

For example, when a defect having the same size is included in both of a circuit pattern having a high density and a circuit pattern having a low density, the circuit pattern having a low density has a higher ratio of the abnormal portion in the measurement region, and thus a measurement value indicating higher abnormality than that of the measurement value of the circuit pattern having a high density is obtained. When the presence or absence of the defect included in the circuit pattern having a plurality of different shapes is accurately determined from measurement values obtained in such a procedure, it is necessary that the threshold value of the defect determination is optimized for each shape of the circuit pattern or the size of the measurement region is optimized for each shape of the circuit pattern, and thus an extremely complicated procedure is required.

Hereinafter, in order to obtain an evaluation result for suitably selecting processing with respect to a semiconductor device, a pattern-measuring apparatus and a semiconductor-measuring system will be described.

Solution to Problem

As an aspect for attaining the object described above, there is proposed a pattern-measuring apparatus including an arithmetic device which compares a circuit pattern of an electronic device with a reference pattern, in which the arithmetic device classifies the circuit pattern in processing unit of the circuit pattern on the basis of a comparison of a measurement result between the circuit pattern and the reference pattern with at least two threshold values.

In addition, as another aspect for attaining the object described above, there is proposed a pattern-measuring apparatus including an arithmetic device which compares a circuit pattern of an electronic device with a reference pattern, in which the arithmetic device classifies a measurement portion on the basis of relationship information of a measurement result between the circuit pattern and the reference pattern, and other layers of the measurement portion of the circuit pattern.

Further, as still another aspect for attaining the object described above, there is proposed a pattern-measuring apparatus including an arithmetic device which compares a circuit pattern of an electronic device with a reference pattern, in which the arithmetic device obtains a process window of an exposure device based on a measurement result of a pattern obtained according to a plurality of exposure conditions with respect to a plurality of patterns, and selects a pattern of the process window defining an outline (a boundary between the inside and the outside of the process window) of a common region of a plurality of process windows obtained with respect to the plurality of patterns as a measurement target pattern.

In addition, there is proposed a semiconductor-measuring system determining a processing process of a circuit pattern by comparing a circuit pattern of an electronic device with a reference pattern, which includes a unit detecting a pattern edge from a captured image of the circuit pattern; a unit measuring an interval between the pattern edge existing in a predetermined measurement region and the reference pattern; a unit selecting a measurement value group of a predetermined pattern length or an area from measurement values of a plurality of portions in the measurement region in order to include a maximum measurement value; a unit calculating a shape score of the circuit pattern from the measurement value group; and a unit determining the processing process of the circuit pattern by comparing the shape score with a predetermined threshold value.

Advantageous Effects of Invention

According to the configuration described above, information for suitably selecting or necessary for selecting processing with respect to a semiconductor device is able to be obtained.

BRIEF DESCRIPTION OF DRAWINGS

FIG. 1 is a flowchart illustrating a procedure of inspection performed by comparing a reference pattern with a pattern edge.

FIG. 2 is a diagram illustrating a configuration of a semiconductor-measuring system.

FIG. 3 is a diagram illustrating the comparison between the reference pattern and the pattern edge.

FIG. 4 is a flowchart illustrating a threshold value determination procedure of a shape score.

FIG. 5 is a flowchart illustrating a procedure of specifying design coordinates of a shape score calculation point.

FIG. 6 is a flowchart illustrating a procedure of narrowing a circuit pattern of a correction target by analyzing patterns of upper and lower layers.

FIG. 7 is a flowchart illustrating a procedure of registering an inspection result in a hot spot library.

FIGS. 8A and 8B are diagrams illustrating a comparison between the inspection result and the patterns of the upper and lower layers.

FIGS. 9A-9F are diagrams illustrating a comparison between the inspection result and the hot spot library.

FIG. 10 is a diagram illustrating a process window.

FIG. 11 is a flowchart illustrating a procedure of narrowing a circuit pattern of a monitoring target by using PWA.

FIG. 12 is a flowchart illustrating a procedure of narrowing the circuit pattern of the monitoring target by using correction history.

FIG. 13 is a diagram illustrating data of the correction history.

FIG. 14 is a diagram illustrating a screen of GUI displaying inspection information.

FIG. 15 is a flowchart illustrating an inspection procedure.

FIG. 16 is a flowchart illustrating a step of setting measurement conditions according to a positional relationship between a measurement target pattern of a measurement target layer and a pattern of the other layer.

FIGS. 17A and 17B are diagrams illustrating an example of setting a measurement box in the measurement target pattern.

FIG. 18 is a flowchart illustrating a step of selecting the measurement target pattern on the basis of measurement of an FEM wafer.

FIG. 19 is a diagram illustrating an example of a pattern-measuring system including a pattern-measuring apparatus.

DESCRIPTION OF EMBODIMENT

An example described below relates to a pattern-measuring apparatus, and for example, relates to a pattern-measuring apparatus which determines the presence or absence of a defect with respect to a circuit pattern having a plurality of different shapes by a unified threshold value, and determines a processing process of the circuit pattern.

In this example, a semiconductor-measuring system determining a processing process of a circuit pattern by comparing a circuit pattern of an electronic device with a reference pattern, which includes a unit detecting a pattern edge from a captured image of the circuit pattern; a unit measuring an interval between the pattern edge existing in a predetermined measurement region and the reference pattern; a unit selecting a measurement value group of a predetermined pattern length from measurement values of a plurality of portions in the measurement region in order to include a measurement value having a maximum interval; a unit calculating a shape score of the circuit pattern from the measurement value group; and a unit determining the processing process of the circuit pattern by comparing the shape score with a predetermined threshold value will be described.

According to the configuration described above, the circuit pattern of the electronic device is compared with the reference pattern, and thus a shape error of both of the patterns is cyclopaedically measured, and the shape score of the circuit pattern is calculated from a plurality of measurement values selected on the basis of a regulation which does not depend on the shape of the circuit pattern such as the pattern length or the area, and thus the defect of the circuit pattern having a plurality of different shapes is able to be determined by the unified threshold value, and then the processing process of the circuit pattern is able to be accurately determined.

Hereinafter, a semiconductor-measuring apparatus which scores the shape of the circuit pattern by comparing the reference pattern with the pattern edge extracted from the captured image, and determines the processing process of the circuit pattern by using the threshold value or the like will be described. In this example, the comparison between the reference pattern and the pattern edge extracted from the captured image, the scoring of the shape, and the determination of the processing process of the circuit pattern are performed as follows.

First, an image of the circuit pattern on a wafer which is suspected of the presence of a systematic defect is captured by an SEM and is input to the semiconductor-measuring system. The coordinates of the systematic defect on the wafer are able to be specified by inspection of a design layout using optical simulation or analysis of the defect which is detected by a bright field inspection device or the like. Next, the pattern edge of the circuit pattern is extracted from the captured image by using edge detection processing or the like.

Next, the reference pattern and the circuit pattern are superposed, and the shape error of the reference pattern and the circuit pattern is measured. The superposition is manually adjusted or automatically adjusted by the pattern matching. The reference pattern is a circuit pattern having a preferred shape, and is defined by the inspection operator. As the reference pattern, a golden pattern which is selected by the inspection operator from a circuit pattern generated by performing the optical simulation with respect to a diagram illustrating the outline of a pattern formed on the basis of design data or a circuit pattern to be actually manufactured, and a circuit pattern which is manufactured in advance is used. As the golden pattern, a circuit pattern in best exposure conditions which is obtained by performing analysis with respect to the process window is able to be used.

The shape of the circuit pattern is deformed into various shapes according to manufacturing conditions of a semiconductor or a circuit layout. In order to accurately grasp the degree of deformation, the measurement region is set in a two-dimensional region including inspection coordinates, and a distance between the reference pattern included in the measurement region and the edge of the circuit pattern is cyclopaedically measured at predetermined intervals. Next, the plurality of measurement values obtained from the measurement region are subjected to statistic processing such as averaging, and a result thereof is set to the measurement value of the measurement region.

In this example, as an aspect for determining a defect of a circuit pattern having a plurality of different shapes by a unified threshold value, and for determining a processing process of a circuit pattern, there is proposed a semiconductor-measuring system determining the processing process of the circuit pattern by comparing a circuit pattern of an electronic device with a reference pattern, which includes a unit detecting a pattern edge from a captured image of the circuit pattern; a unit measuring an interval between the pattern edge existing in a predetermined measurement region and the reference pattern; a unit selecting a measurement value group of a predetermined pattern length from measurement values of a plurality of portions in the measurement region in order to include a maximum measurement value; a unit calculating a shape score of the circuit pattern from the measurement value group; and a unit determining the processing process of the circuit pattern by comparing the shape score with a predetermined threshold value.

In addition, in the example described below, an example of a semiconductor-measuring system determining a processing process of a circuit pattern of an electronic device by comparing the circuit pattern with a reference pattern, which includes a unit detecting a pattern edge from a captured image of the circuit pattern; a unit measuring an interval between the pattern edge existing in a predetermined measurement region and the reference pattern; a unit selecting a measurement value group of a predetermined area from measurement values of a plurality of portions in the measurement region in order to include a maximum measurement value; a unit calculating a shape score of the circuit pattern from the measurement value group; and a unit determining the processing process of the circuit pattern by comparing the shape score with a predetermined threshold value will be also described.

In addition, in the example described below, an example of the semiconductor-measuring system will be also described in which the threshold value is a threshold value for determining the abnormality and the normality of the circuit pattern.

In addition, in the example described below, an example of the semiconductor-measuring system will be described in which the threshold value is two threshold values for determining the normality of the circuit pattern, a reticle/mask correction target, and a monitoring target at the time of high-volume production.

In addition, in the example described below, an example of the semiconductor-measuring system which further includes a unit obtaining design coordinates corresponding to a portion of the circuit pattern in which the shape score is calculated will be described.

In addition, in the example described below, an example of the semiconductor-measuring system which further includes a unit comparing the portion of the circuit pattern in which the shape score is calculated with design information, calculating the criticality of the circuit pattern, and selecting a reticle/mask correction target will be described.

In addition, in the example described below, an example of the semiconductor-measuring system which further includes a unit comparing the design information corresponding to the circuit pattern which is determined as abnormal with database of a danger point, and registering the design information in the database when the design information is not registered in the database will be described.

In addition, in the example described below, an example of the semiconductor-measuring system which further includes a unit obtaining a process window with respect to a plurality of circuit patterns which are determined as abnormal, and determining two or more circuit patterns limiting a maximum focus, a minimum focus, a maximum dose, and a minimum dose as a monitoring target at the time of high-volume production will be described.

In addition, in the example described below, an example of the semiconductor-measuring system which further includes a unit retaining history information of the circuit pattern which is a reticle/mask correction target, and determining a circuit pattern of a monitoring target at the time of high-volume production on the basis of the history will be described.

In addition, in the example described below, an example of the semiconductor-measuring system which further includes an electron scanning microscope forming image data on the basis of an electron obtained by scanning an electronic device with an electron beam will be described.

In addition, in the example described below, an example of the semiconductor-measuring system which further includes a screen displaying at least one data item of the portion of the circuit pattern in which the shape score is calculated, design coordinates of the portion of the circuit pattern in which the shape score is calculated, the shape score, the correction history, a processing process determination defect, a process window analysis result, design coordinates of a circuit pattern which is a reticle/mask correction target, a diagram of a circuit pattern which is a reticle/mask correction target, design coordinates of a circuit pattern which is a monitoring target at the time of high-volume production, and a diagram of a circuit pattern which is a monitoring target at the time of the high-volume production will be described.

The circuit pattern of the electronic device is compared with the reference pattern, and thus the shape error of both of the patterns is cyclopaedically measured, and the shape score of the circuit pattern is calculated from the plurality of measurement values specified on the basis of a regulation which does not depend on the shape of the circuit pattern such as the pattern length or the area, and thus the defect of the circuit pattern having a plurality of different shapes is able to be determined by the unified threshold value, and then the processing process of the circuit pattern is able to be accurately determined.

Hereinafter, a semiconductor-measuring apparatus which scores the shape of a circuit pattern by comparing a reference pattern with a circuit pattern extracted from a captured image, and determines a processing process of the circuit pattern by using a threshold value or the like will be described.

FIG. 2 is a schematic configuration diagram of a semiconductor-measuring system. The semiconductor-measuring system includes a scanning electron microscope 201 (Scanning Electron Microscope: hereinafter, referred to as SEM) acquiring image data of a circuit pattern, and a control device 202 inspecting the circuit pattern by analyzing the image data. The SEM 201 applies an electron ray 202 to a specimen 203 such as a wafer from which an electronic device is manufactured, a secondary electron detector 204 and reflection electron detectors 205 and 206 capture an electron discharged from the specimen 203, and an A/D converter 207 converts the electron into a digital signal. The digital signal is input into a control device 202 and is stored in a memory 208, image processing is performed by a CPU 209 or image processing hardware 210 such as ASIC and FPGA according to the purpose, and thus the circuit pattern is inspected.

Further, the control device (an arithmetic device) 202 is connected to a display 211 including an input unit, and has a function of Graphical User Interface (GUI) displaying an image, an inspection result, and the like with respect to a user. Furthermore, a part of all of the control of the control device 202 is able to be processed and controlled by being allocated to a CPU, an electronic computer provided with a memory which is able to accumulate an image, and the like. In addition, the control device 202 is connected to a capturing recipe preparation device 212 which prepares coordinates of the electronic device necessary for the inspection, a template for matching the pattern used in inspection positioning, and a capturing recipe including capturing conditions or the like manually or by using design data 213 of the electronic device, through a network, a bus, or the like.

FIG. 19 is a diagram illustrating an example of a pattern-measuring system including the pattern-measuring apparatus. This system mainly includes an electron scanning microscope main body 1901, a control device 1902 controlling the electron scanning microscope main body 1901, a pattern-measuring apparatus 1903 transmitting necessary information to the control device 1902 and forming a process window of an exposure device on the basis of a signal acquired by the electron scanning microscope main body 1901 and on the basis of the measurement of the pattern formed on the specimen or a measurement result thereof, a design data storage medium 1904 storing design data of a semiconductor device, and an input device 1905 for inputting necessary information. In the example of FIG. 19, an example is described in which the pattern-measuring apparatus is disposed separately from the electron scanning microscope, and the pattern measurement may be performed by the arithmetic device disposed in the electron scanning microscope. Furthermore, in this example, an example is described in which the SEM is applied as a capturing device, but the configuration is not limited thereto, and for example, a focused ion beam device forming a scan image on the basis of a signal obtained by scanning a focused ion beam on the specimen is able to be used as the capturing device.

An arithmetic device 1906 in the pattern-measuring apparatus 1903 includes a measurement condition setting unit 1908 setting conditions necessary for the measurement, a measurement value arithmetic unit 1909 measuring a dimension between edges on the basis of the signal obtained by the electron scanning microscope main body 1901, a process window preparation unit 1910 classifies a pattern measurement result at the time of measuring a FEM wafer on the basis of a predetermined threshold value and generating a process window on the basis of focus conditions and dose conditions of the pattern included in the predetermined threshold value, and a pattern selection unit 1911 selecting a pattern which is a measurement target. In addition, in the pattern-measuring apparatus 1903, a memory 1907 for storing the measurement conditions set by the measurement condition setting unit 1908 as a recipe is embedded. In the memory 1907, the measurement result obtained by the measurement value arithmetic unit 1906, the process window prepared by the process window preparation unit 1910, and the like are stored in addition to the measurement recipe.

In addition, the design data stored in the design data storage medium 1904, for example, is expressed in a GDS format, an OASIS format, and the like, and is stored in a predetermined format. Furthermore, the design data may be expressed in any format insofar as the format is able to be displayed by software displaying the design data and is able to be treated as diagram data.

FIG. 15 is a flowchart illustrating a measuring step of a semiconductor pattern. First, the operator sets the inspection (measurement) conditions by using the recipe preparation device 212 and the pattern-measuring apparatus 1903 (Step 1501). The inspection conditions include the capturing magnification of the SEM 201, the coordinates of the circuit pattern (hereinafter, referred to as inspection coordinates), a measurement region, an inspection method (an inspection method, the measurement of dimension, and the like described below), parameters necessary for the inspection, and the like, and are information for acquiring a captured image of the circuit pattern which is an inspection target by the SEM 201 and for inspecting the captured image. The inspection coordinates are the coordinates of a reticle or a wafer in which the occurrence of a defect obtained by optical simulation is expected, and the coordinates of a reticle or a wafer in which the occurrence of the defect is confirmed by an exterior appearance inspection device or the like.

Such inspection coordinates are supplied to the capturing recipe preparation device 212 from a device 214 expecting the defect by using the optical simulation, a device 215 generating the inspection coordinates based on the exterior appearance inspection device of the wafer, and the like. The measurement region is coordinate information of a two-dimensional region which is set to surround the inspection coordinates, and is determined by the inspection operator.

Next, the capturing recipe is generated (Step 1502). The capturing recipe is data for controlling the SEM 201, and in the capturing recipe, a template for specifying the inspection conditions set by the inspection operator or the like and an inspection point from the captured image is defined. Next, on the basis of the recipe, the SEM 201 captures the image of the circuit pattern (Step 1503). Next, an inspection point in the captured image is specified by performing pattern matching (Step 1504). Next, the circuit pattern is measured by using a method described below (Step 1505). Finally, the processing process of the circuit pattern is determined by using a measurement value (Step 1506). The determination of the processing process is performed by comparing the measurement value according to the inspection of the present invention with the predetermined threshold value determined by the inspection operator, and by analyzing the circuit pattern described below.

FIG. 14 illustrates a GUI screen 1400 of the inspection result. This GUI screen 1100 is displayed on a screen of the display 211, the capturing recipe generation device 212, or the CPU or the electronic computer provided with the memory which is able to accumulate the image in which a part of all of the control of the control device 202 is allocated by using a GUI program. The GUI program is stored in the memory of the semiconductor-measuring apparatus, and is executed by being processed by the CPU of the semiconductor-measuring apparatus.

The semiconductor-measuring apparatus displays a reference pattern 1402, a circuit pattern 1403, and a measurement region 1404 on a circuit pattern display window 1401 of the GUI screen 1400 on the basis of the inspection result. In addition, the measurement value or the determination result is displayed on the inspection result window 1404. In addition, various inspection parameters are displayed on the inspection parameter window 1406.

A determination procedure of a more specific processing process of the circuit pattern (normal (nothing is performed thereto), correcting a design layout or a mask, performing monitoring at the time of high-volume production) will be described with reference to FIG. 1 and FIG. 3. FIG. 1 is a flowchart illustrating a processing process determination procedure. First, the captured image of the circuit pattern suspected of the presence of the systematic defect which is specified by the analysis of the optical simulation or the exterior appearance inspection device is input (Step 101). The reference pattern is a circuit pattern having a shape which is a manufacturing target, and for example, is a golden pattern which is selected by the inspection operator from the design data, a circuit pattern generated by performing the simulation with respect to a circuit pattern to be actually manufactured, and a circuit pattern which is manufactured. The reference pattern is stored in the capturing recipe or in the memory disposed in the semiconductor-measuring apparatus.

Next, the pattern edge included in the captured image is extracted (Step 102). The reference pattern is compared with the shape of the pattern edge included in the captured image, and thus both of the reference pattern and the pattern edge are superposed, and a shape error of the reference pattern and the pattern edge is measured. FIG. 3 illustrates a superposition result of a reference pattern 301 and a pattern edge 302. A superposed position may be determined by using a result of the pattern matching which is performed before the inspection, or may be performed again by a pattern matching algorithm which is more accurate than that before the inspection.

Next, a distance 306 between the reference pattern 301 and the pattern edge 302 positioned in a measurement region 300 is measured (Step 103). In order to accurately grasp various shape deformations, measurement points are set on the reference pattern (or on the pattern edge) at an interval in pixel unit or sub-pixel unit, and the interval in both of the pixel unit and the sub-pixel unit is cyclopaedically measured. The pattern matching, the measurement processing, and the like as described above may be executed by dedicated hardware, or the processing described above or processing described below may be executed by a general computer.

Furthermore, the measurement points are set at predetermined or arbitrary intervals, and set a measurement direction towards a predetermined direction from the measurement point (for example, a fixed direction, a direction allocated to each portion of the pattern, a direction perpendicular to the edge of the reference pattern 301, and the like), and a corresponding point set not to intersect with a straight line connecting the other measurement point and a point corresponding thereto, which is a point on the pattern edge 302 closest to the measurement point or a point on the pattern edge 302 closest from the measurement. In addition, the measurement direction is not limited to that described above, and the measurement direction may be set according to predetermined conditions different from those described above. The measurement direction is able to be automatically set according to the conditions or the like described above.

Furthermore, one of objects of measuring the distance between the reference pattern and the pattern edge is to obtain a shape difference between both of the reference pattern and the pattern edge, and thus it is preferable to obtain a distance between corresponding points before and after the deformation, and for this reason, it is preferable that the measurement direction is set by using the point on the pattern edge 302 closest to the measurement point disposed in the reference pattern 301 as the corresponding point. However, the measurement direction is able to be set by using a predetermined regulation (for example, the measurement direction is set to be included in a predetermined angle range) such that an erroneous corresponding point is not detected due to an influence of unexpected deformation of the circuit pattern or noise.

Next, a plurality of measurement values are selected from a plurality of measurement values obtained by the distance measurement of a plurality of portions in the measurement region 300 on the basis of parameters which do not depend on the shape (Step 104). The parameters which do not depend on the shape are parameters indicating a pattern length or a pattern area. Specifically, only a measurement value which is measured in a zone of a designated pattern length 304 is extracted from the plurality of measurement values in the measurement region 300. For example, in the measurement region 300, an edge point 303 on the reference pattern having the longest distance with respect to the pattern edge is specified, the zone of the pattern length 304 is set to include the edge point 303, and the plurality of measurement values are selected. Accordingly, the plurality of measurement values focused on a portion of the circuit pattern having a large shape difference with respect to the reference pattern are able to be selected. Furthermore, it is not necessary that a zone for selecting the measurement value is continuous. The measurement value of the zone of the designated pattern length may be selected from the plurality of measurement values obtained in the measurement region 300 in descending order.

Alternatively, a measurement value existing in an area 305 based on area parameters in which the edge point 303 on the reference pattern having the longest distance with respect to the pattern edge in the measurement region 300 is set in the center is selected. Next, a shape score is calculated from the selected measurement value (Step 105). The shape score is obtained by the average of the extracted measurement values, and by a statistic arithmetic operation of a standard deviation or the like. Finally, the threshold value of the calculated shape score is determined, and thus the processing process of the circuit pattern is determined (Step 106).

FIG. 4 is a flowchart illustrating a threshold value determination procedure of the shape score. In this example, an example will be mainly described in which on the basis of a comparison between the measurement result of the circuit pattern and the reference pattern and at least two threshold values, the circuit pattern is classified in processing unit of the circuit pattern (for example, classification of whether the circuit pattern is a correction processing target of the design data or a later monitoring target (a measurement target) even through the correction is not performed). Hereinafter, the shape score will be described as the circuit pattern in which a relationship of an abnormal circuit pattern>a normal circuit pattern is satisfied. First, the shape score is compared with a threshold value TH1 (Step 401). The circuit pattern having a shape score which is less than the threshold value TH1 is determined as normal (Step 402). The shape score is compared with a threshold value TH2 (Step 403), and the circuit pattern having a shape score greater than or equal to the threshold value TH2 as a correction target of the design layout or the mask (Step 404). The circuit pattern having a shape score greater than the threshold value TH1 and less than or equal to the threshold value TH2 is determined as a monitoring target at the time of high-volume production (Step 405). These determination results are stored in the memory 208. Furthermore, the threshold values TH1 and TH2 are determined by a design tolerance or are experimentally determined.

In order to perform each processing with respect to the design layout or the mask correction, and the circuit pattern which is the monitoring target at the time of the high-volume production, accurate design coordinates of a correction portion and monitoring portion are necessary. For this reason, by adding a procedure illustrated in FIG. 5 to the flowchart illustrated in FIG. 1, the design coordinates corresponding to the portion of the circuit pattern in which the shape score is calculated are able to be obtained. First, the captured image of the circuit pattern and a design pattern used for manufacturing the circuit pattern are subjected to the pattern matching, and a corresponding relationship between the design pattern and the image is obtained (Step 501). Furthermore, when the pattern matching is performed by using the design pattern as a template at the time of capturing the image, the corresponding relationship between the design pattern and the image obtained as above is used. Next, the portion of the reference pattern in which the measurement value used for calculating the shape score is obtained is specified (Step 502). When the measurement value based on shape independent parameters is extracted, the image coordinates of the edge in which the measurement value is obtained are registered in the memory 208, and thus the portion of the reference pattern in which the measurement value is able to be easily specified. Next, the design coordinates corresponding to the portion of the reference pattern are obtained by a corresponding relationship between the design pattern and the circuit pattern which is obtained by the pattern matching (Step 503).

In addition, a circuit pattern having high criticality is able to be specified from the circuit patterns which are determined as a target of the design layout or the mask correction by comparing the threshold values of the shape score. FIG. 6 illustrates a procedure. First, the captured image of the circuit pattern and the design pattern used for manufacturing the circuit pattern are subjected to the pattern matching, and a corresponding relationship between the design pattern and the image is obtained (Step 601). Furthermore, when the pattern matching is performed by using the design pattern as a template at the time of capturing the image, the corresponding relationship between the design pattern and the image obtained as above is used. Next, the portion of the circuit pattern in which the measurement value used for calculating the shape score is obtained is specified (Step 602). When the measurement value based on shape independent parameters is extracted, the image coordinates of the edge in which the measurement value is obtained are registered in the memory 208, and thus the portion of the reference pattern in which the measurement value is able to be easily specified. Next, a positional relationship between the design pattern and the circuit pattern is obtained based on a corresponding relationship between the image obtained by the pattern matching and the design pattern.

As illustrated in (a) and (b) of FIG. 8, an example will be described in which design patterns 801 of a wiring layer which is an inspection target are homozygous, and via positions 802 and 805 of a via layer which is connected to a lower portion of the wiring layer are different from each other. In this example, an example will be described in which the measurement portion is classified on the basis of the measurement result between the circuit pattern and the reference pattern, and relationship information between the measurement portion of the circuit pattern and the other layer. In the example of (a) of FIG. 8, a wiring portion of the circuit pattern 803 in which a via is not formed is retracted from a reference pattern 804. In the example of (b) of FIG. 8, a wiring portion of the circuit pattern 803 in which the via is formed is retracted from the reference pattern 804. In such a case, the criticality is higher in (b) than in (a) of FIG. 8. The retraction amount of the wiring of the circuit pattern with respect to the reference pattern is the same, and thus the criticality varies according to the design layout. For this reason, for example, in the design coordinates corresponding to the portion of the circuit pattern, the presence or absence of upper and lower vias is detected, and thus the shape difference with respect to the reference pattern increases, but the circuit pattern which is not required to be corrected is able to be excluded from the correction target.

As described above, for example, even in the patterns having the same shape, the pattern is divided into a pattern in which the deformation of the pattern is allowed to some extent and a pattern in which the deformation of the pattern is required to be severely controlled according to the positional relationship with respect to the pattern of the other layer. For example, (a) of FIG. 17 is a diagram illustrating an end portion of a pattern 1701 and layout data of a pattern to which a via 1702 is connected, and (b) of FIG. 17 is a diagram illustrating layout data of the end portion of the pattern 1701 to which the via is not connected. As described above, in (b) of FIG. 17, even when a line end is slightly retracted, a defect such as a breakage of a part of a circuit does not occur. In contrast, in (a) of FIG. 17, when the line end is retracted, the connection with respect to the via 1702 may be broken. Accordingly, in the pattern in (a) of FIG. 17, a layout/mask correction target portion or a monitoring target portion is determined, and thus the yield ratio of the semiconductor device is able to be rapidly improved compared to the pattern in (b) of FIG. 17.

FIG. 16 is a flowchart illustrating a step of setting measurement conditions for obtaining the degree of dissociation between the design data and an actual pattern edge (for example, an edge in an SEM image and outline data in which the edge is outlined) on the basis of the threshold value determination. First, the measurement condition setting unit 1908 reads the layout data of the layer which is a measurement target from the design data storage medium 1904 or the like, and sets a measurement box 1703 on the read layout data (Steps 1601 and 1602). The measurement box 1703 defines a measurement region having a dimension between the reference pattern and the edge of the SEM image and the outline data obtained from the SEM image. Further, in this example, a superposed pattern determination region 1704 is set as accessory information of the measurement box 1703.

Next, the layout data of the layer including the pattern connected to a pattern of a measurement target layer is read (Step 1603). The pattern selection unit 1911 determines whether or not a pattern (for example, the via 1702) other than the pattern of the measurement target layer is included in the superposed pattern determination region 1704 (Step 1604), and when the pattern other than the pattern of the measurement target layer is not included as exemplified in (b) of FIG. 17, for example, the measurement is not performed or measurement conditions are selected as a normal monitoring target. In addition, as exemplified in (a) of FIG. 17, when the pattern of the other layer is included in the superposed pattern determination region, by comparing the pattern of the other layer with the normal monitoring target, measurement conditions are selected as a low threshold value or a priority control portion (Steps 1605 and 1606).

As described above, the selected measurement conditions are registered in the memory 1907 or the like as a recipe which is an operation program of the SEM, and thus suitable measurement conditions according to a connection state of the pattern of the other layer is able to be set.

In FIG. 17, the step of setting the measurement conditions by using the layout data is described, and the method as described above may be used at the time of determining a semiconductor evaluation portion in a high-volume production line on the basis of edge information from an actual SEM image. Specifically, even in a portion which is determined as normal, a pattern having a relationship with respect to the pattern of the other layer is considered as a monitoring evaluation target. In addition, it is considered that measurement conditions are set such that a pattern evaluation is performed with respect to the pattern which is originally selected as the monitoring target portion on a basis of a stricter evaluation reference. A lower threshold value is set as the measurement conditions by comparing the pattern with the normal monitoring target pattern, and thus a portion having a risk of disconnection is able to be subjected strict dimension control.

Furthermore, as the deformation of the pattern, two deformations such as expansion in which the area of the pattern increases and retraction in which the area of the pattern decreases are considered, and the retraction is mainly concerned about disconnection from the via of the other layer, and thus simple threshold value determination is not performed but determination of whether the deformation is the expansion or the retraction is performed, and in a case of the retraction, the pattern may be selectively selected as a monitoring target or a pattern based on a stricter evaluation reference.

In addition, information of the circuit pattern which is determined as a correction target is useful information of circuit design. In the circuit design, the circuit layout which is automatically generated is corrected by using information of a danger point of the circuit pattern which is referred to as a Hot Spot Library (hereinafter, referred to as a HSL) accumulated in the design of the past. For this reason, when the layout of the circuit pattern which is the correction target is not registered in the HSL, DB registration of the HSL is performed. The procedure is illustrated in FIG. 7.

First, the captured image of the circuit pattern and the design pattern used for manufacturing the circuit pattern are subjected to the pattern matching, and thus the corresponding relationship between the design pattern and the image is obtained (Step 701). Furthermore, when the pattern matching is performed by using the design pattern as a template at the time of capturing the image, the corresponding relationship between the design pattern and the image obtained herein is used. Next, the portion of the reference pattern in which the measurement value used for calculating the shape score is obtained is specified (Step 702). The coordinates of the portion of the reference pattern is used as the center, the design layout having the same pattern size as that of the HSL is specified and is cut out on the basis of the corresponding relationship between the image and the design pattern which is obtained by the pattern matching, and is compared with the database of the HSL (Step 703).

FIG. 9 illustrates an example of HSLs (a), (b), (c), and (d), and design layouts (e) and (f) corresponding to the circuit pattern of the inspection target. Regions 903 and 904 of the design layout having the same size as that of the HSL is cut out by using measurement points 901 and 902 in which the shape score is obtained as the center, and each of the regions 903 and 904 is compared with the HSLs (a), (b), (c), and (d). The comparison is performed by comparing the cutout design layout with the design layout of HS registered in the HSL using the pattern matching. The cutout design layout 903 has high degree of similarity with the HSL (a). On the other hand, the cutout design layout 904 is not similar to any HSL. When the similarity with the cutout design layout is less than or equal to a predetermined numerical value, the design layout is registered in the database of the HSL as new HS (Step 704). In the example of FIG. 9, the cutout design layout (e) is registered in the database of the HSL.

In addition, circuit patterns suitable for a monitor are further limited from a plurality of circuit patterns which are determined as a monitoring target according to the threshold value determination of the shape score, and thus an inspection time relevant to the monitor is able to be suppressed. The procedure will be described with reference to the flowcharts of FIG. 10 and FIG. 11. In this example, an example will be described in which the process window of the exposure device based on the measurement result of the pattern obtained by a plurality of exposure conditions is obtained with mainly respect to the plurality of patterns, and the pattern of the process window defining the outline (the boundary between the inside and the outside of the process window) of a common region of a plurality of process windows obtained with respect to the plurality of patterns is selected as a measurement target pattern.

FIG. 10 is a diagram illustrating process windows of five circuit patterns which are determined as a monitoring target by the analysis of the shape score. The process window indicates a range of two parameters of a focus amount and a dose amount of the exposure device in which a non-defective product is able to be manufactured. The process window is specified by manufacturing chips which are manufactured by gradually changing the value of the two parameters on a wafer, and by performing measurement and specification determination with respect to a circuit pattern of each of the chips. A semiconductor which is resistant to a fluctuation in the exposure conditions is able to be manufactured as the process window becomes wider, and thus in the stage of development of the semiconductor, measures for enlarging the process window to the maximum extent are used. For this reason, at the time of the high-volume production, the circuit pattern which is a factor of narrowing the process window is monitored. The wafer used for specifying the process window will be described as a Focus-Exposure-Matrix (FEM) wafer, and the procedure of specifying the process window will be described as Process Window Analysis (PWA). Furthermore, the measurement and the specification determination of the circuit pattern are performed by using a dimension value of the pattern or a shape error value between the reference pattern and the circuit pattern as illustrated in FIG. 3.

First, the FEM image of the circuit pattern which is determined as a monitoring target is input (Step 1101). The number of images is the number of circuit patterns determined as the monitoring target×the number of exposure conditions for performing the PWA (the number of focus steps×the number of dose steps). The PWA is performed by using these images, and process windows 1000, 1001, 1002, 1003, and 1004 of the respective circuit patterns are obtained (1102). Four circuit patterns limiting the minimum/maximum point of the focus amount and the maximum/minimum point of the dose amount are specified by focusing on a common region 1009 of the process windows 1000, 1001, 1002, 1003, and 1004 of the respective circuit patterns (Step 1103). At the time of focusing on the dose amount, a limitation point of the common region 1009 is the process windows 1007 and 1008, and each of the process windows 1004 and 1002 is the factor of narrowing the common region 1009. In addition, at the time of focusing on the focus amount, the limitation point of the common region is the process windows 1005 and 1006, each of the process windows 1001 and 1003 is the factor of narrowing the common region 1009. Four circuit patterns corresponding to the process windows 1001, 1002, 1003, and 1004 which are factors of narrowing the common region 1009 of the process window, or circuit patterns including these four circuit patterns are determined as a monitor pattern (Step 1104).

FIG. 18 is a flowchart more specifically illustrating the step of selecting the measurement target pattern on the basis of the measurement of the FEM wafer. The FEM wafer is introduced to a specimen chamber of the SEM (Step 1801), and then a plurality of different patterns is measured in each of the plurality of exposure conditions (Step 1802). The FEM wafer is obtained by being patterned by sequentially changing the conditions of the focus and the dose of the exposure device in order to set the conditions of the exposure device, and thus the chip is measured to the extent of grasping a boundary between a chip which is able to be determined as at least a non-defective product and a chip which is not able to be determined as a non-defective product according to the threshold value determination or the like. Basically, on the design data arranged on a different chip, the same pattern is set to a measurement target. In addition, in this example, in order to form a plurality of process windows, different types of patterns are measured.

Next, a process window for each of the measurement target pattern is prepared on the basis of the measurement result for each of the chips of a plurality of measurement target patterns (Step 1804). A plurality of process windows prepared in this way are superposed as illustrated in FIG. 10, a common region of each of the process windows is extracted (Step 1804). The pattern selection unit 1911 selects a pattern of a process window forming the outline of the common region, or a pattern forming the upper and lower limits of the focus and the dose of the common region (Step 1805), and in the measurement condition setting unit 1908, the selected pattern or a plurality of patterns including these patterns are set to a measurement target and are registered as a recipe (Step 1806). At this time, a target pattern may be displayed on a display device of the input device 1905 by using the selected pattern as a measurement target candidate, and the operator may select a measurement target pattern.

According to the method exemplified in FIG. 18, for example, this is particularly effective when the number of measurement target candidates is 20 and the number of measurement target candidates is desired to be reduced to 10, or when a pattern for performing suitable evaluation is desired to be selected from the randomly determined measurement target candidates.

In addition, in the plurality of circuit patterns which are determined as the monitoring target at the time of the high-volume production by determining the shape score, the circuit pattern is able to be determined as the monitoring target at the time of the high-volume production by using the number of times of the correction of the design layout or the mask. The procedure is illustrated in FIG. 12. The circuit pattern in which the number of times of the correction of the design layout or the mask increases is more likely to be a circuit pattern which is rarely manufactured, and thus a decrease in the yield ratio is able to be prevented by preferentially selecting and monitoring such a circuit pattern.

First, in all of the circuit patterns which are determined as the monitoring target at the time of the high-volume production by determining the shape score, the circuit patterns are arranged in descending order of the number of times of the correction with reference to the number of times of the correction of the design layout or the mask (Step 1201). The history of the number of times of the correction is data in which the circuit pattern inspected as illustrated in FIG. 13 is able to be specified, and is stored in the memory 208 at the time of executing the processing process determination 106 illustrated in FIG. 1. Next, a predetermined number of circuit patterns from the high rank of the number of times of the correction is determined as a monitoring target (Step 1202).

REFERENCE SIGNS LIST

201 SEM
202 ELECTRON RAY
203 SPECIMEN
204 SECONDARY ELECTRON DETECTOR
205 REFLECTION ELECTRON DETECTOR
1,206 REFLECTION ELECTRON DETECTOR
2,207 A/D CONVERTER
208 MEMORY
209 CPU
210 HARDWARE
211 DISPLAY UNIT
212 RECIPE GENERATION SYSTEM
213 DESIGN DATA
214 EDA SYSTEM
215 EXTERIOR APPEARANCE INSPECTION DEVICE
301 REFERENCE PATTERN
302 PATTERN EDGE OF CIRCUIT PATTERN
303 MEASUREMENT REPRESENTATIVE POINT
304 PATTERN ZONE
305 MEASUREMENT AREA HAVING MEASUREMENT REPRESENTATIVE POINT IN CENTER
306 INTERVAL BETWEEN REFERENCE PATTERN AND PATTERN EDGE
801 DESIGN PATTERN

802 VIA
803 PATTERN EDGE OF CIRCUIT PATTERN
804 REFERENCE PATTERN
805 VIA
806 PATTERN EDGE OF CIRCUIT PATTERN
901 SHAPE SCORE CALCULATION POINT
902 SHAPE SCORE CALCULATION POINT
903 CUTOUT AREA OF DESIGN LAYOUT
904 CUTOUT AREA OF DESIGN LAYOUT
1000 TO 1004 PROCESS WINDOW OF CIRCUIT PATTERN
1005 TO 1008 COMMON REGION LIMITATION POINT OF PROCESS WINDOW
1009 COMMON REGION OF PROCESS WINDOW
1400 GUI FOR DESIGNATING INSPECTION PARAMETER
1401 REFERENCE PATTERN DISPLAY WINDOW
1402 REFERENCE PATTERN
1403 PATTERN EDGE OF CIRCUIT PATTERN
1404 MEASUREMENT REGION
1405 INSPECTION RESULT WINDOW
1406 INSPECTION PARAMETER SETTING WINDOW

The invention claimed is:

1. A semiconductor-measuring system determining a processing process of a circuit pattern of an electronic device by comparing the circuit pattern of the electronic device with a reference pattern, the system comprising:
processing circuitry and a non-transitory memory storing a program which, when executed by the processing circuitry, causes the processing circuitry to:
detect a pattern edge from a captured image of the circuit pattern;
measure an interval between the pattern edge existing in a predetermined measurement region and the reference pattern;
select a measurement value group of a predetermined pattern length or an area from measurement values of a plurality of portions in the measurement region in order to include a maximum measurement value;
calculate a shape score of the circuit pattern from the measurement value group based on a characteristic of the circuit pattern that is independent of a shape of the circuit pattern; and
determine the processing process of the circuit pattern by comparing the shape score with a predetermined threshold value, including comparing the shape score to a first threshold value to determine whether the circuit pattern is normal wherein the circuit pattern is determined to be normal when the shape score is less than the first threshold value, and when the shape score is greater than or equal to the first threshold value, the shape score is compared to a second threshold value, wherein when the shape score is greater than or equal to the second threshold value, the circuit pattern is determined to be a reticle/mask correction target, and when the shape score less than the second threshold value, the circuit pattern is determined to be a monitoring target at a time of high-volume production;
wherein the processing circuitry obtains a process window with respect to a plurality of circuit patterns which are determined as abnormal, and determines two or more circuit patterns limiting a maximum focus, a minimum focus, a maximum dose, and a minimum dose as a monitoring target at a time of high-volume production.

2. The semiconductor-measuring system according to claim 1,
wherein the processing circuitry compares design information corresponding to the circuit pattern which is determined as abnormal with a database of a danger point, and registers the design information in the database when the design information is not registered in the database.

3. The semiconductor-measuring system according to claim 1,
wherein the processing circuitry obtains design coordinates corresponding to a portion of the circuit pattern in which the shape score is calculated.

4. The semiconductor-measuring system according to claim 1,
wherein the processing circuitry compares a portion of the circuit pattern in which the shape score is calculated with design information, calculates criticality of the circuit pattern, and selects the reticle/mask correction target.

5. The semiconductor-measuring system according to claim 1,
wherein the processing circuitry retains history information of the circuit pattern which is the reticle/mask correction target, and determines the circuit pattern of the monitoring target at a time of high-volume production on the basis of the history.

6. The semiconductor-measuring system according to claim 1, further comprising:
an electron scanning microscope forming image data on the basis of an electron obtained by scanning an electronic device with an electron beam.

7. The semiconductor-measuring system according to claim 6, further comprising:
a screen displaying at least one data item of a portion of the circuit pattern in which the shape score is calculated, design coordinates of the portion of the circuit pattern in which the shape score is calculated, the shape score, a correction history, a processing process determination defect, a process window analysis result, design coordinates of a circuit pattern which is a reticle/mask correction target, a diagram of a circuit pattern which is the reticle/mask correction target, design coordinates of a circuit pattern which is a monitoring target at the time of high-volume production, and a diagram of a circuit pattern which is a monitoring target at a time of the high-volume production.

* * * * *